US008562513B2

(12) United States Patent
Yamatani

(10) Patent No.: US 8,562,513 B2
(45) Date of Patent: Oct. 22, 2013

(54) ENDOSCOPE DEVICE

(75) Inventor: Ken Yamatani, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 927 days.

(21) Appl. No.: 12/123,742

(22) Filed: May 20, 2008

(65) Prior Publication Data

US 2009/0292164 A1 Nov. 26, 2009

(51) Int. Cl.
A61B 1/00 (2006.01)
(52) U.S. Cl.
USPC .............................. 600/106; 600/107; 600/129
(58) Field of Classification Search
USPC ................... 600/106–107, 173–174
See application file for complete search history.

(56) References Cited

U.S. PATENT DOCUMENTS

| 4,763,662 | A | * | 8/1988 | Yokoi | 600/461 |
|---|---|---|---|---|---|
| 5,653,677 | A | * | 8/1997 | Okada et al. | 600/112 |
| 6,352,503 | B1 | * | 3/2002 | Matsui et al. | 600/104 |
| 6,648,816 | B2 | * | 11/2003 | Irion et al. | 600/173 |
| 7,066,879 | B2 | * | 6/2006 | Fowler et al. | 600/102 |
| 7,654,951 | B2 | * | 2/2010 | Ishikawa | 600/114 |
| 2005/0085691 | A1 | * | 4/2005 | Nakao | 600/128 |
| 2005/0096502 | A1 | * | 5/2005 | Khalili | 600/106 |
| 2005/0234294 | A1 | | 10/2005 | Saadat et al. | |
| 2006/0183975 | A1 | * | 8/2006 | Saadat et al. | 600/139 |
| 2006/0189845 | A1 | * | 8/2006 | Maahs et al. | 600/146 |
| 2007/0167679 | A1 | | 7/2007 | Miyamoto et al. | |
| 2007/0167680 | A1 | | 7/2007 | Miyamoto et al. | |
| 2007/0249897 | A1 | | 10/2007 | Miyamoto et al. | |
| 2007/0255100 | A1 | | 11/2007 | Barlow et al. | |

FOREIGN PATENT DOCUMENTS

| JP | H06-066615 | U | 9/1994 |
| JP | S63-294508 | A | 12/1998 |
| JP | H11-276419 | A | 10/1999 |
| JP | 2000-210249 | A | 8/2000 |
| JP | 2005-312903 | A | 11/2005 |
| WO | 99/42028 | A | 8/1999 |

OTHER PUBLICATIONS

Notice of Reasons for Rejection dated Jan. 29, 2013 from corresponding Japanese Patent Application No. 2009-121854 together with an English language translation.

* cited by examiner

Primary Examiner — Matthew J Kasztejna
(74) Attorney, Agent, or Firm — Scully, Scott, Murphy & Presser, P.C.

(57) ABSTRACT

An endoscope device comprising: an elongated tubular insertion part; a plurality of arm members which is provided in the distal portion of the insertion part so as to protrude forward and is capable of treatment with a treatment tool inserted thereinto; an observation main body provided in the distal portion of the insertion part so as to freely separate from the insertion part; an energization member which energizes the observation main body disposed within the distal portion of the insertion part toward the direction opposite to the plurality of the arm members in the radial direction of the insertion part; and a holding mechanism which resists the energization member to hold the observation main body in a state where the observation main body is disposed within the distal portion of the insertion part and is capable of releasing the holding state.

1 Claim, 18 Drawing Sheets

ENDOSCOPE DEVICE

BACKGROUND OF THE INVENTION

1. Field of the Invention

The present invention relates to an endoscope device which is inserted into the body cavity and is used together with a device such as a flexible endoscope.

2. Description of Related Art

Conventionally, endoscope devices are used for observing and treating an affected area or the like within the body cavity of the subject. Endoscope devices are known in which an elongated and flexible insertion part which is inserted into the body cavity from the distal side, and an operating part for operating the insertion part are provided so as to connect to each other.

The distal portion of the insertion part is provided with an observation main body for observing the periphery, and a distal end construction part on the distal end surface of which two arm members into which treatment tools for performing treatment are inserted are provided. A bendable tuber bending part is connected to the proximal side of the distal end construction part, and a flexible tuber part which is connected with an operating part is connected to the proximal side of the bending part. A distal portion of an operating wire inserted into the bending part and the flexible tuber part is fixed to the proximal side of the distal end construction part, and the proximal portion of the operating wire is attached to an angle knob which is provided in the operating part and pulls the operating wire.

Instrument channels are formed so as to extend from the distal portions of the two arm members to a forceps plug provided in the operating part via the insertion part. By inserting the treatment tools into the instrument channels, treatment can be performed with the distal portions of the treatment tools protruded from the distal ends of the arm members.

In the endoscope device constituted as above, the insertion part is inserted into the body cavity of the subject while observing the periphery by using the observation main body and bending the bending part by using the angle knob so that the distal portions of the treatment tools do not protrude from the distal ends of the two arm members. Then, the insertion part is fixed so that the two arm members are opposed to the affected area and the distal end portions of the treatment tools are protruded from the distal ends of the arm members to perform treatment.

However, with the above-described conventionally endoscope devices, since the distance between the observation main body and the proximal ends of the two arm members is short, the proximal portions of the two arm members extensively appear on the field of view via the observation main body. As a result, it is difficult to observe the state of treatment performed by the treatment tools by using the observation main body. When making the distance between the observation main body and the proximal ends of the two arm members large, since the diameter of the insertion part also becomes large, the insertion ability reduces.

SUMMARY OF THE INVENTION

The present invention was devised in view of the above circumstances, and has as an object the provision of an endoscope device in which depression of the insertion ability of the insertion part is prevented and visibility of the distal portions of the arm members when performing treatment is enhanced.

The present invention relates to an endoscope device comprising: an elongated tubular insertion part; a plurality of arm members which is provided in the distal portion of the insertion part so as to protrude forward and is capable of treatment with a treatment tool inserted thereinto; an observation main body provided in the distal portion of the insertion part so as to freely separate from the insertion part; an energization member which energizes the observation main body disposed within the distal portion of the insertion part toward the direction opposite to the plurality of the arm members in the radial direction of the insertion part; and a holding mechanism which resists the energization member to hold the observation main body in a state where the observation main body is disposed within the distal portion of the insertion part and is capable of releasing the holding state.

DETAILED DESCRIPTION OF THE INVENTION

Embodiments according to the present invention will now be described in detail below. The basal structures of endoscope devices according to the present invention have been described in U.S. patent application Ser. No. 11/331,963, U.S. patent application Ser. No. 11/435,183, and U.S. patent application Ser. No. 11/652,880, and the described contents of which are incorporated in the following description.

First Embodiment

Figure 1:
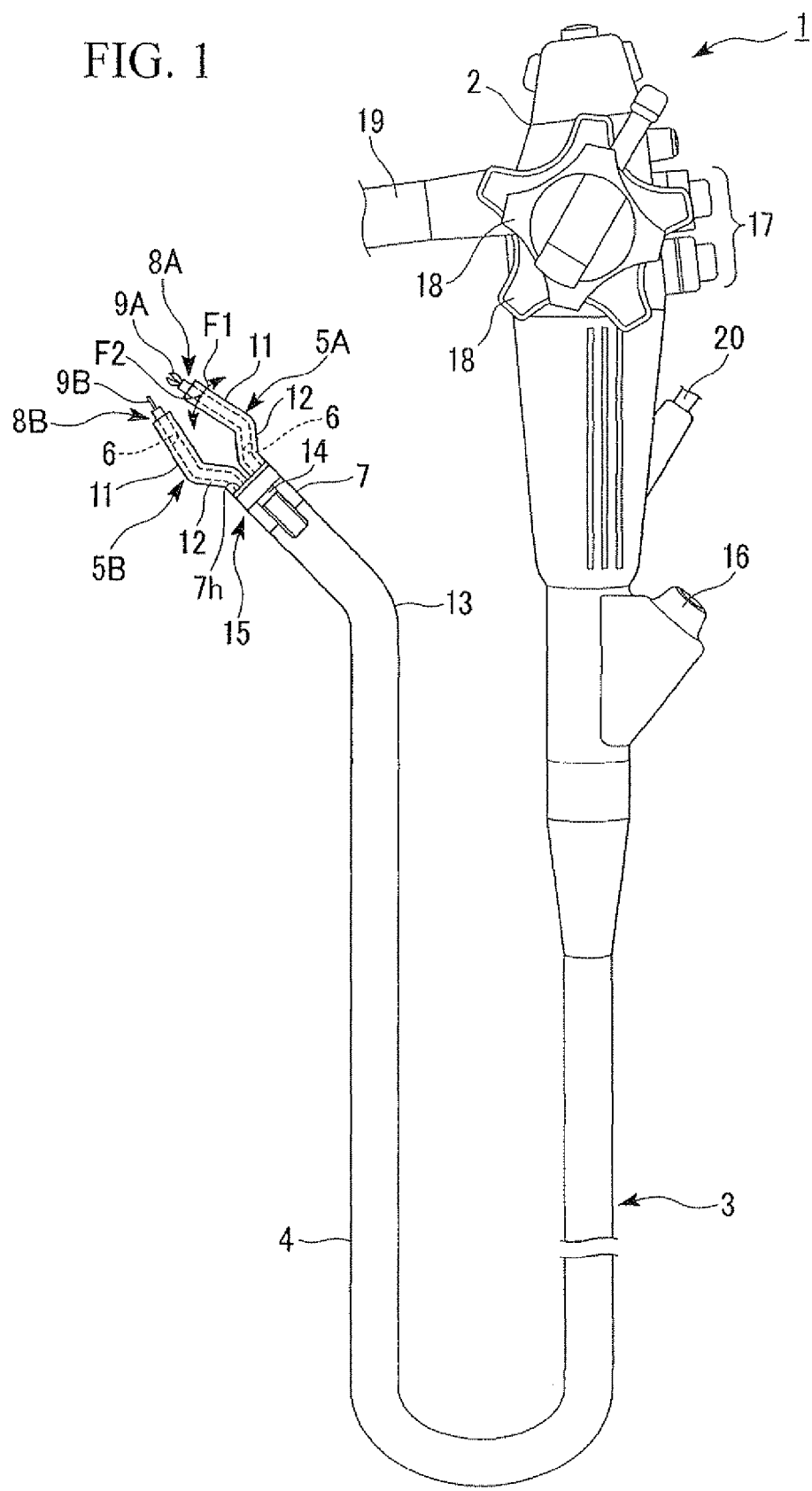
FIG. 1 is an overall view showing an endoscope device according to a first embodiment of the present invention.

As shown in FIG. 1, an endoscope device 1 has an operating part 2 and a tubular insertion part 3 which extends from one end of the operating part 2 in a unitary manner. The insertion part 3 is elongated and has flexibility. The insertion part 3 has the same construction as an insertion part described in U.S. patent application Ser. No. 11/435,183 or U.S. patent application Ser. No. 11/652,880. That is, the insertion part 3 has a sheath 4, a distal end construction part 7 which is disposed in the distal portion of the sheath 4, and bendable first and second arm members 5A and 5B which are provided on a distal end surface 7h of the distal end construction part 7 so as to protrude forward. Instrument channels 6 are formed inside the arm members 5A and 5B respectively, and extend to connect with a later-described connection sheath 20 via the insertion part 3 and operating part 2. Treatment tools 8A and 8B are inserted into the instrument channels 6 respectively, and treatment parts 9A and 9B of the treatment tools 8A and 8B protrude from the distal portions of the arm members 5A and 5B respectively. According to these treatment tools 8A and 8B, the first and second arm members 5A and 5B can perform treatment within the body cavity.

A first bending part 11 and a second bending part 12 are formed in each arm member 5A and 5B in order from the distal side. Bending operation within the body cavity can be performed by moving the first and second bending parts 11 and 12 together with a third bending part 13 formed in the insertion part 3.

An observation main body 14 for observing inside the body is disposed on the outer circumferential surface of the distal portion of the distal end construction part 7 so as to be capable of separating from the insertion part 3. The observation main body 14 is held by a holding mechanism 15.

The first and second arm members 5A and 5B may be inserted into another sheath protruding from the distal end of the sheath 4, as described in U.S. patent application Ser. No. 11/652,880.

A forceps plug 16 is provided in the operating part 2 at the side surface of the one end portion connecting to the insertion part 3. The forceps plug 16 communicates with the instrument channels 6 formed within the sheath 4. By inserting a second treatment tool (not shown) from the forceps plug 16, the second treatment tool can be protruded from the distal end of first or second arm member 5A or 5B. The operating part 2 is further provided with a switch 17, an angle knob 18, and a universal cable 19 which is connected to a control device or a monitor (not shown). The switch 17 is operated, for example, when feeding air or water, or aspirating through the instrument channel 6 formed within the insertion part 3. The angle knob 18 is used when bending the third bending part 13 in all directions with respect to the axis. An image observed by the observation main body 14 is transmitted to the monitor via the universal cable 19.

Figure 2:
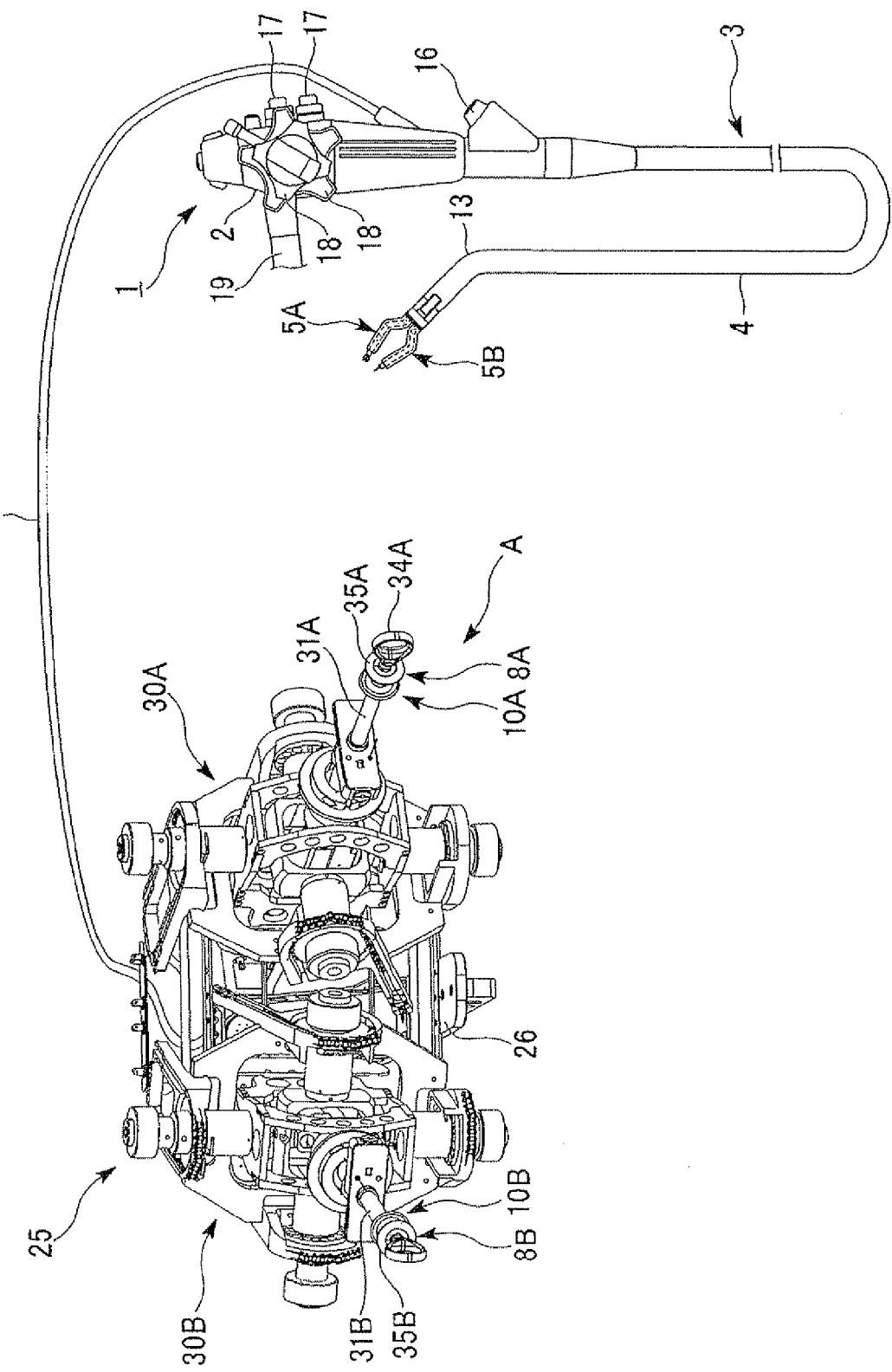
FIG. 2 is an overall view showing a medical treatment endoscope in which the endoscope device according to the first embodiment of the present invention is attached.

As shown in FIG. 2, the elongated and flexible connecting sheath 20 is provided so as to extend from the other end portion of the operating part 2. An operator 25 is provided at the end portion of the connection sheath 20.

The operator 25 has a base 26 which fixes the connection sheath 20. A first operating unit 30A and a second operating unit 30B are attached with respect to the base 26. The first operating unit 30A has an operating stick 31A into which an operating part 10A of the treatment tool 8A inserted into the first arm member 5A is inserted. The operating part 10A is supported via the operating stick 31A so as to freely advance and retract in the axial direction and to freely lean in all directions about the axis. The second operating unit 30B has an operating stick 31B into which an operating part 10B of the treatment tool 8B inserted into the first arm member 5B is inserted. The operating part 10B is supported via the operating stick 31B so as to freely advance and retract in the axial direction and to freely lean in all directions about the axis.

Figure 3:
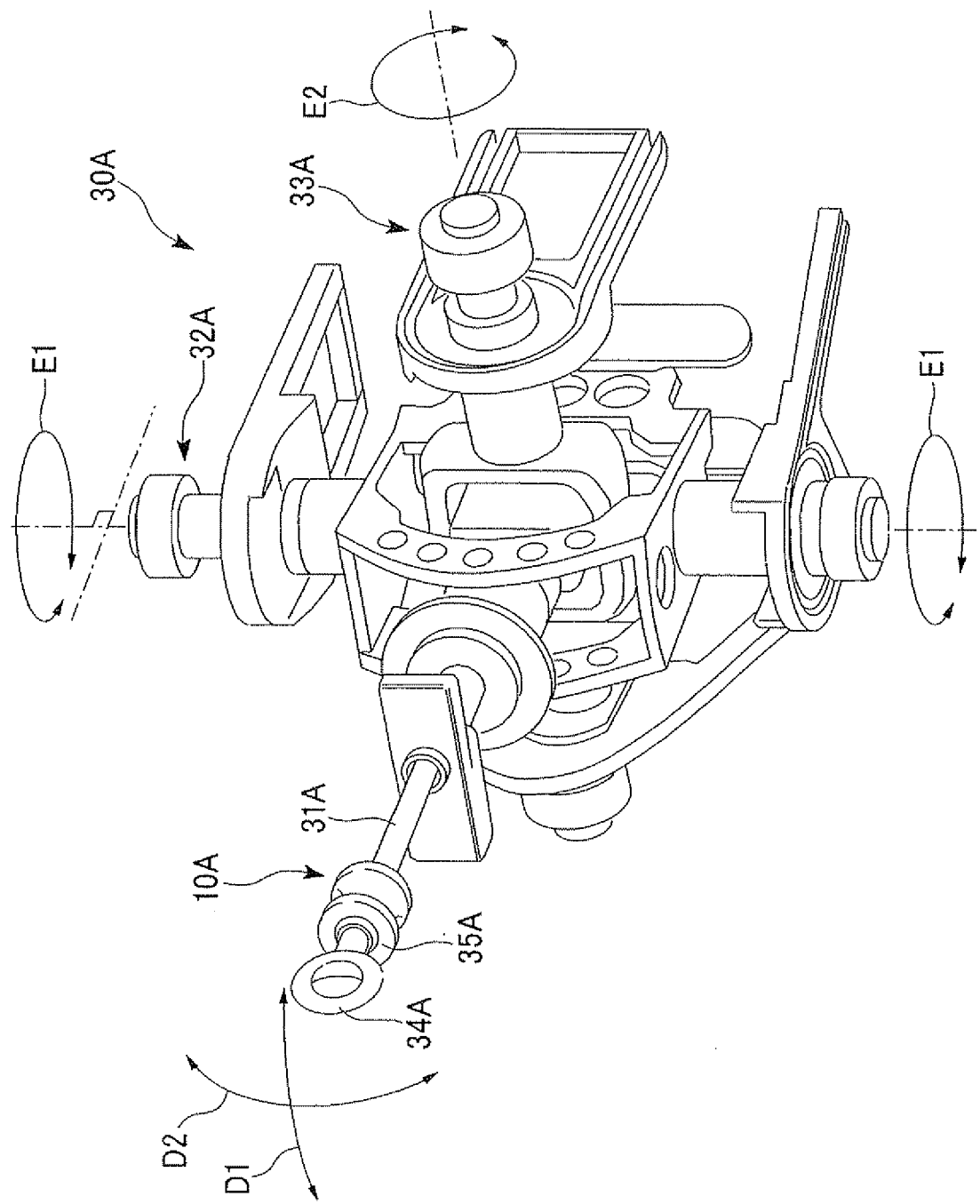
FIG. 3 illustrates a view seen from the arrow A in FIG. 2.

By the known constitution shown in FIG. 3, when the operator rotates the operating stick 31A to the direction D1, the first rotation mechanism 32A rotates to the direction E1. As a result, the first bending part 11 of the first arm member 5A is bent to the direction F1 as shown in FIG. 1 by an operating wire (not shown) wound on the first rotation mechanism 32A. When the operator rotates the operating stick 31A to the direction D2, the second rotation mechanism 33A rotates to the direction E2. As a result, the first bending part 11 of the first arm member 5A is bent to the direction F2 orthogonal to the direction F1 (i.e., the direction orthogonal to the sheet) by an operating wire (not shown) wound on the second rotation mechanism 33A.

Although the detailed explanation is omitted, the first bending part 11 of the second arm member 5B is similarly bent when an operating stick 31B shown in FIG. 2 is rotated.

When an operating lever (not shown) is pushed, the second bending parts 12 of the first and second arm members 5A and 5B are straight and the arm members 5A and 5B protrude forward in the linear shape from the distal end surface 7h of the distal end construction part 7. By pulling and then fixing the operating lever, as shown in FIG. 1, the second bending parts 12 are maintained in the curbed shape in a state where the first and second arm members 5A and 5B are separated from each other.

In the present embodiment, a gripping forceps is employed as the treatment tool 8A and an injection instrument is employed as the treatment tool 8B. As shown in FIG. 3, the opening/closing operation of the distal portion of this gripping forceps is performed by moving a slider 35A with respect to a ring 34A in the axial direction to pull and push an operating wire (not shown) connected to the treatment part 9A. On the other hand, when injecting by the injection instrument of the treatment part 9B into the tissue, as shown in FIG. 2, a slider 35 provided in the second operating unit 30 B is operated. Though in this embodiment, a gripping forceps and an injection instrument are employed as the treatment tools 8A and 8B, this invention is not limited thereto and, for example, other treatment tools such as a high-frequency treatment tool, scissors, or a high-frequency snare may be employed.

Figure 4:
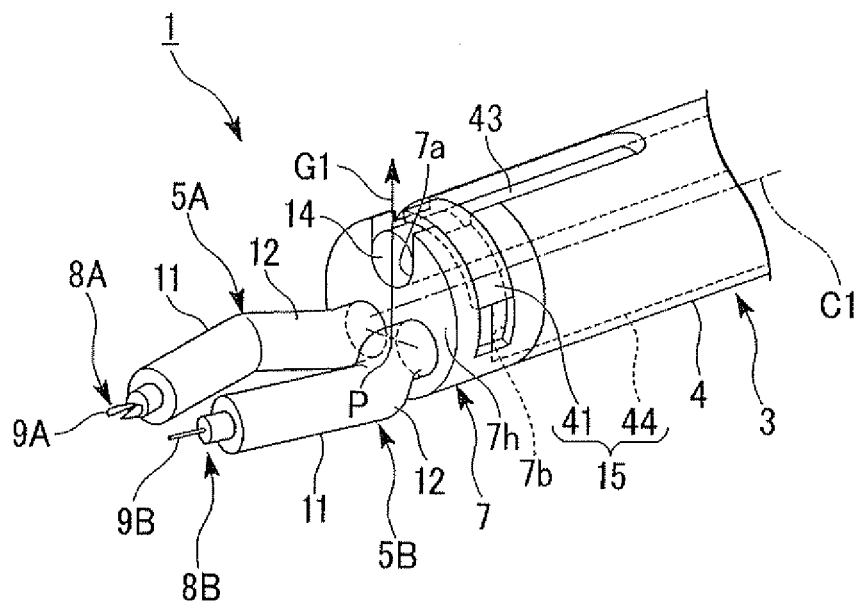
FIG. 4 shows an insertion part of the endoscope device according to the first embodiment of the present invention.

As shown in FIG. 4, a first groove 7a is formed along the axis C1 of the insertion part 3 on the outer circumferential surface of the distal end construction part 7, and the observation main body 14 is disposed within the first groove 7a. The observation main body 14 houses a light receiving element such as a lens and a CCD, and connects to an observation cable 43 which transmits an image obtained by the observation main body 14 to the monitor. The observation cable 43 has a bending tendency and plays a role as an energizing member which energizes the observation main body 14 disposed in the first groove 7a toward the moving direction G1 opposite to the first and second arm members 5A and 5B in the radial direction of the insertion part 3. The observation cable 43 is guided by a guide hole (not shown) communicating from the distal end construction part 7 of the insertion part 3 to the operating part 2.

Here, as shown in FIG. 4, the opposite side of the first and second arm members 5A and 5B in the radial direction of the insertion part 3 means a symmetrical side with the midpoint P between the positions where the first and second arm members 5A and 5B are provided on the distal end surface 7h of the distal end construction part 7, with respect to the axis C1.

A second groove 7b is formed along the circumferential direction on the outer circumferential surface of the distal end construction part 7, and a curved plate-shaped open/close member 41 is supported by the second groove 7b so as to freely move along the circumferential direction of the distal end construction part 7. As shown in FIG. 4, the open/close member 41 is set such that, when moving to one side of the second groove 7b, the open/close member 41 resists the energizing force by the observation cable 43 to hold the observation main body 14 in a state where the observation main body 14 is disposed within the first groove 7a, and, when moving from the position shown in FIG. 4 to the other side of the second groove 7b, the holding state of the observation main body 14 is released. Both end portions of the open/close member 41 are connected to an open/close member driving wire 44. The open/close member driving wire 44 is guided by the guide hole (not shown) communicating from the distal end construction part 7 of the insertion part 3 to the operating part 2, and is operated by a field main body operating lever (not shown) provided in the operating part 2.

The open/close member 41 and the open/close member driving wire 44 constitute the above-described holding mechanism 15.

Method for treating an affected area with the endoscope device 1 constituted as above is described as follows.

First, the operating lever is pushed such that the first and second arm members 5A and 5B are parallel to each other. Then, the treatment tools 8A and 8B are pulled with respect to the operating parts 10A and 10B to make the treatment parts 9A and 9B be in a state where the treatment parts 9A and 9B do not protrude from the distal ends of the arm members 5A and 5B.

Next, the periphery is observed by the observation main body 14, and the insertion part 3 is inserted into the body cavity of the subject while bending the first bending portions 11 of the arm members 5A and 5B by using the first and second operating units 30A and 30B respectively and bending the third bending part 13 by using the angle knob 18.

Next, the insertion part 3 is fixed in a state where the distal portions of the two arm members 5A and 5B are opposed to the affected area. Then, the treatment tools 8A and 8B are pushed with respect to the operating parts 10A and 10B such that the treatment parts 9A and 9B of the treatment tools 8A and 8B are protruded from the distal ends of the arm members 5A and 5B as shown in FIG. 4. By pulling and then fixing the operating lever, the second bending parts 12 are fixed in a bending state where the first and second arm members 5A and 5B are separated from each other.

Figure 5:
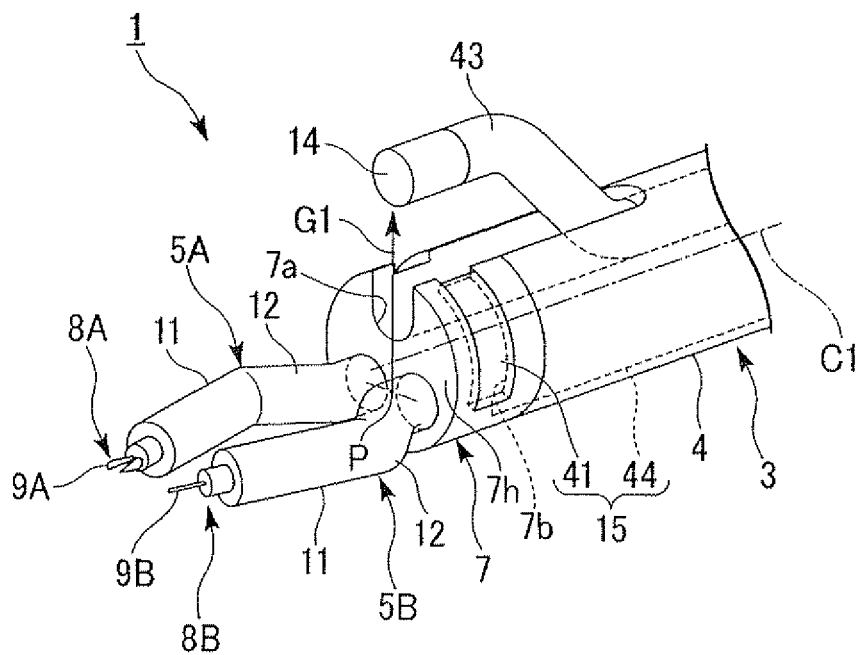
FIG. 5 shows a treatment method with the endoscope device according to the first embodiment of the present invention.

Next, as shown in FIG. 5, by operating the open/close member driving wire 44 by using the field main body operating lever, the open/close member 41 is moved to the other side of the second groove 7b to release the holding state of the observation main body 14. As a result, since the observation cable 43 energizes the observation main body 14 disposed in the first groove 7a toward the moving direction G1, the observation main body 14 is moved to a position separating from the distal end construction part 7 while maintaining the posture of the observation main body 14.

In this state, while observing the affected area with the observation main body 14, the affected area is grasped by the treatment part 9A by rotating the operating stick 31A to bend the first bending part 11 of the first arm member 5A and by moving the slider 35A. Then, the needle-shaped treatment part 9B is pricked into the affected area while bending the first bending part 11 of the second arm member 5B by rotating the operating stick 31B, and the drug solution or the like (not shown) is injected into the affected area by moving the slider 35B.

When the treatment of the affected area has been finished, in the same manner as when inserting the insertion part 3 into the body cavity, the operating lever is pushed such that the first and second arm members 5A and 5B are parallel to each other. Then, the treatment tools 8A and 8B are pulled with respect to the operating parts 10A and 10B to make the treatment parts 9A and 9B in a state where the treatment parts 9A and 9B do not protrude from the distal ends of the arm members 5A and 5B. Then, the observation main body 14 is housed within the sheath 4 by pulling the observation cable 43 toward the proximal end. After making the insertion part 3 in this state, the insertion part 3 is pulled toward the proximal end so as to be pulled out from the body cavity.

As described above, according to the endoscope device 1 of the present embodiment, the first and second arm members 5A and 5B are provided on the distal end surface 7h of the distal end construction part 7, and the observation main body 14 is disposed within the first groove 7a. Therefore, since the outer diameter of the insertion part 3 including the arm members 5A and 5B can be reduced, the depression of the insertion ability of the insertion part 3 when inserting the insertion part 3 into the body cavity of the subject can be prevented.

Furthermore, since the observation main body 14 is moved to a position separating from the distal end construction part 7 while maintaining the posture of the observation main body 14, the treatment parts 9A and 9B can be observed from the skew direction, not from the proximal side of the first and second arm members 5A and 5B. As a result, since it can be prevented that the field of view via the observation main body 14 is interrupted by the proximal portions of the first and second arm members 5A and 5B when performing treatment, visibility of the treatment parts 9A and 9B can be improved.

Furthermore, since the distance from the treatment parts 9A and 9B to the observation main body 14 can be elongated, the range of view of the treatment parts 9A and 9B via the observation main body 14 can be enlarged. As a result, the treatment of the affected area can be securely performed in brief time.

Next, a modification example of the first embodiment of the present invention will be described. Elements the same as those of the first embodiment are denoted by the same reference numerals and the descriptions thereof are omitted, and only different points are described.

Figure 6:
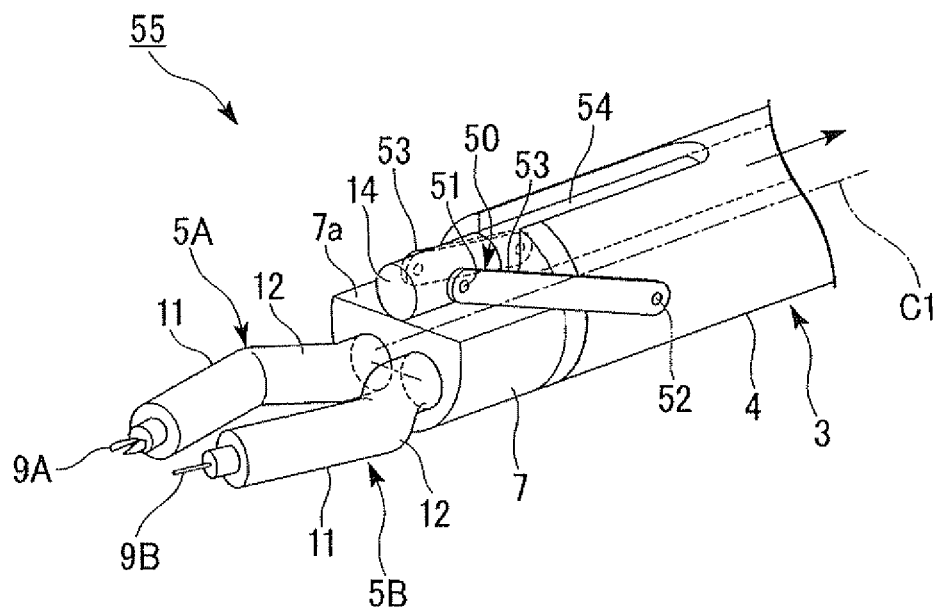
FIG. 6 shows an insertion part of an endoscope device according to a modification example of the first embodiment of the present invention.

As shown in FIG. 6, an endoscope device 55 of the present modification example is provided with a moving mechanism 50 which moves the observation main body 14. The moving mechanism 50 has a pair of link members 53 which are symmetrically disposed so as to sandwich the observation main body 14 therebetween with one end portion of the link member 53 rotatively supported to the observation main body 14 by a first pin 51, and the other end portion of the link member 53 rotatively supported to the insertion part 3 by a second pin 52.

The second pin 52 is disposed such that the axis of the second pin 52 is positioned closer to the axis C1 than the axis of the first pin 51. An observation cable 54 of the present modification example does not have a bending tendency.

Next, a method for treating an affected area with the endoscope device 55 constituted as above is described as follows.

Figure 7:
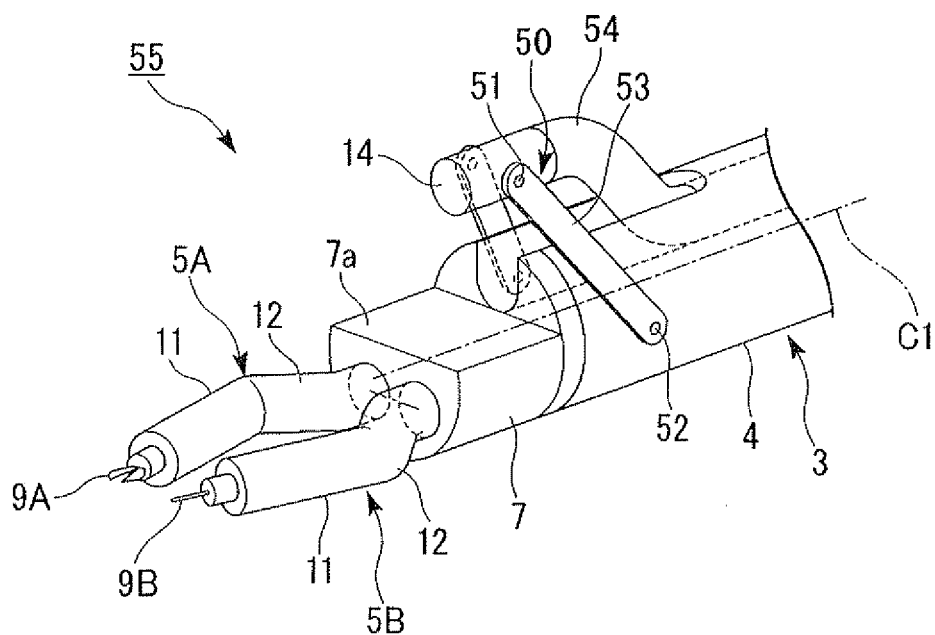
FIG. 7 shows a treatment method with the endoscope device according to the modification example of the first embodiment of the present invention.

The treatment method of the present modification example is basically the same as that of the first embodiment. However, in the present modification example, as shown in FIG. 7, the observation cable 54 inserted into a guide hole (not shown) is moved toward the proximal end by pulling the observation cable 54 toward the proximal end at the operating part 2 after the second bending parts 12 of the first and second arm members 5A and 5B are fixed in a bending state. The observation main body 14 is moved to a position separating from the distal end construction part 7 by rotating the pair of the link members 53 around the second pin 52.

As described above, according to the endoscope device 55 of the present modification example, the same effects as those of the first embodiment can be obtained.

Second Embodiment

Next, a second embodiment of the present invention will be described. Elements the same as those of the first embodiment and the modification example thereof are denoted by the same reference numerals and the descriptions thereof are omitted, and only different points are described.

Figure 8:
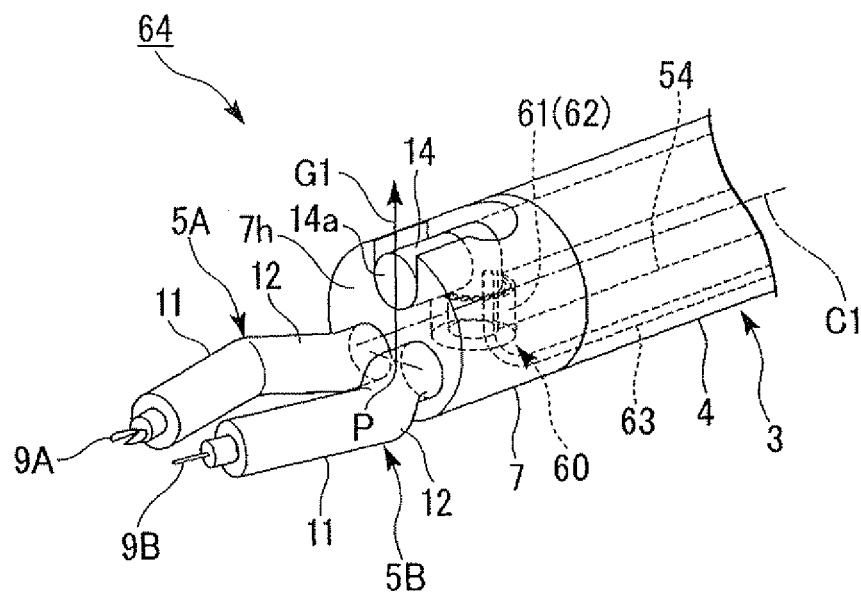
FIG. 8 shows an insertion part of an endoscope device according to a second embodiment of the present invention.

As shown in FIG. 8, an endoscope device 64 of the present embodiment is provided with an extension/contraction mechanism 60 which moves the observation main body 14 toward the moving direction G1 opposite to the first and second arm members 5A and 5B in the radial direction. The extension/contraction mechanism 60 has a telescopic portion 62 formed by nesting a plurality of cylindrical members 61 having diameters different from each other such that the entirety of the telescopic portion 62 freely extends and contracts in the moving direction G1, and an operating wire 63 which protrudes and retracts the telescopic portion 62 in the moving direction G1 by pushing and pulling the proximal portion of the operating wire 63. In the present embodiment, it is preferable that the distal end surface 7h of the distal end construction part 7 and a distal end surface 14a of the observation main body 14 be coplanar.

Next, a method for treating an affected area with the endoscope device 64 constituted as above is described as follows.

Figure 9:
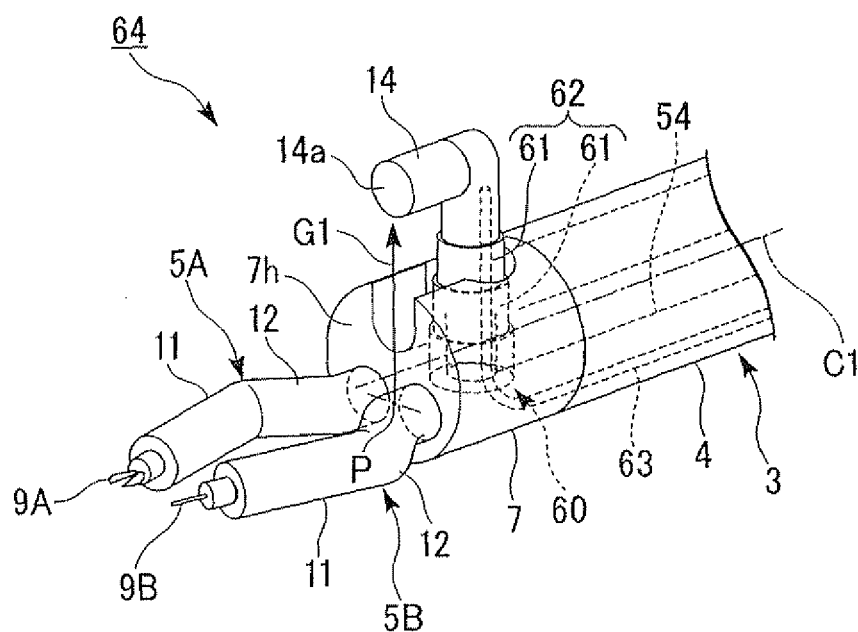
FIG. 9 shows a treatment method with the endoscope device according to the second embodiment of the present invention.

The treatment method of the present embodiment is basically the same as that of the first embodiment. However, in the present embodiment, as shown in FIG. 9, the observation main body 14 is moved toward the moving direction G1 so as to separate from the distal end construction part 7 by pushing the proximal portion of the operating wire 63 after the second bending parts 12 of the first and second arm members 5A and 5B are fixed in a bending state respectively.

As described above, according to the endoscope device 64 of the present embodiment, since the observation main body 14 is moved toward the moving direction G1 so as to separate from the distal end construction part 7, the treatment parts 9A and 9B can be observed from the slew direction, not from the proximal side of the first and second arm members 5A and 5B. As a result, since it can be prevented that the field of view via the observation main body 14 is interrupted by the proximal portions of the first and second arm members 5A and 5B when performing treatment, visibility of the treatment parts 9A and 9B can be improved.

Next, a modification example of the second embodiment of the present invention will be described. Elements the same as those of the second embodiment are denoted by the same reference numerals and the descriptions thereof are omitted, and only different points are described.

Figure 10:
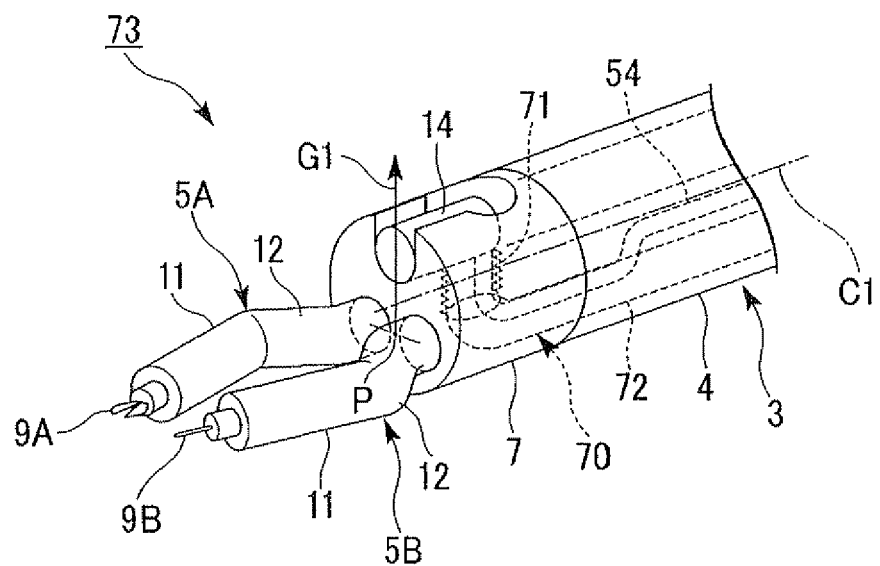
FIG. 10 shows an insertion part of an endoscope device according to a modification example of the second embodiment of the present invention.

As shown in FIG. 10, an endoscope device 73 of the present embodiment is provided with an extension/contraction mechanism 70 which moves the observation main body 14 toward the moving direction G1 opposite to the first and second arm members 5A and 5B in the radial direction. The extension/contraction mechanism 70 has an accordion member 71 formed so as to freely extend and contract in the moving direction G1, and an air pipe 72 connected to an air feeding/exhausting device (not shown) for feeding air to the accordion member 71 and exhausting air from the accordion member 71. The observation cable 54 is connected to the monitor via the accordion member 71, the insertion part 3, and the universal cable 19.

Next, a method for treating an affected area with the endoscope device 73 constituted as above is described as follows.

Figure 11:
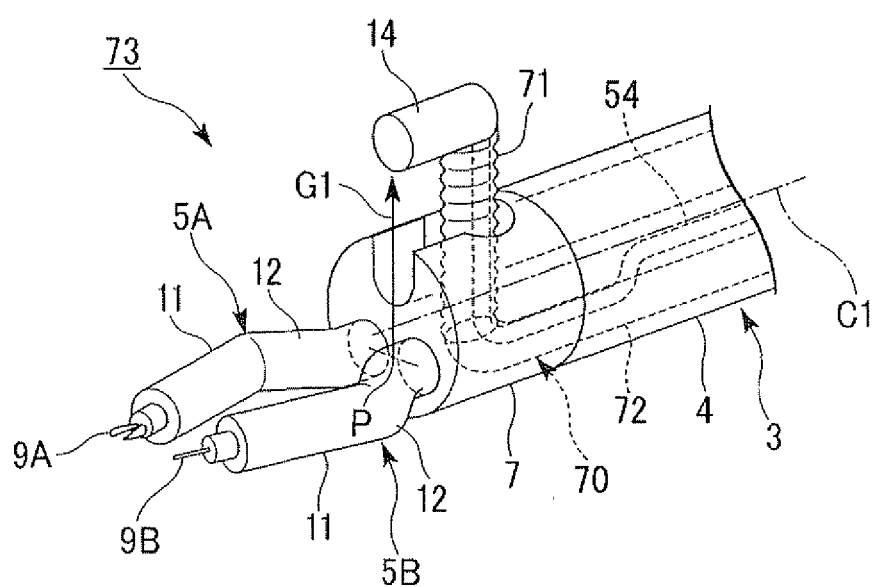
FIG. 11 shows a treatment method with the endoscope device according to the modification example of the second embodiment of the present invention.

The treatment method of the present modification example is basically the same as that of the first embodiment. However, in the present modification example, as shown in FIG. 11, after the second bending parts 12 of the first and second arm members 5A and 5B are fixed in a bending state respectively, the observation main body 14 is moved to a position separating from the axis C1 while maintaining the posture of the observation main body 14 by feeding air to the accordion member 71 via the air pipe 72 by using the air feeding/exhausting device.

As described above, according to the endoscope device 73 of the present modification example, the same effects as those of the second embodiment can be obtained.

Third Embodiment

Next, a third embodiment of the present invention will be described. Elements the same as those of the first and second embodiments and the modification examples thereof are denoted by the same reference numerals and the descriptions thereof are omitted, and only different points are described.

Figure 12:
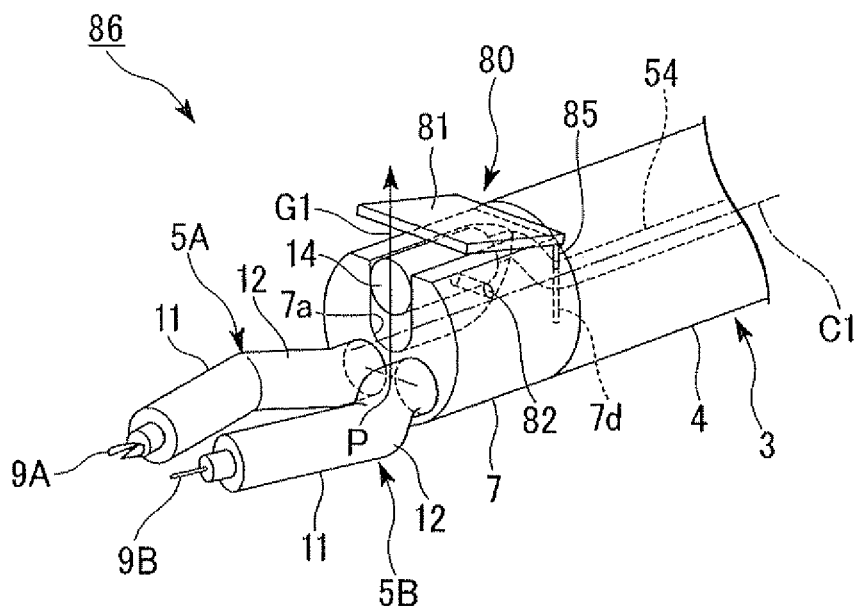
FIG. 12 shows an insertion part of an endoscope device according to a third embodiment of the present invention.

As shown in FIG. 12, an endoscope device 86 of the present embodiment is provided with an observation main body 14 which observes the direction to which the observation main body faces, an observation main body rotation mechanism 80 which rotatively supports the observation main body 14 such that the observation main body 14 faces the moving direction G1 opposite to the first and second arm members 5A and 5B in the radial direction and faces the front of the insertion part 3, and a reflection member 81 disposed in the distal portion of the insertion part 3 so as to freely protrude and retract.

Figure 13:
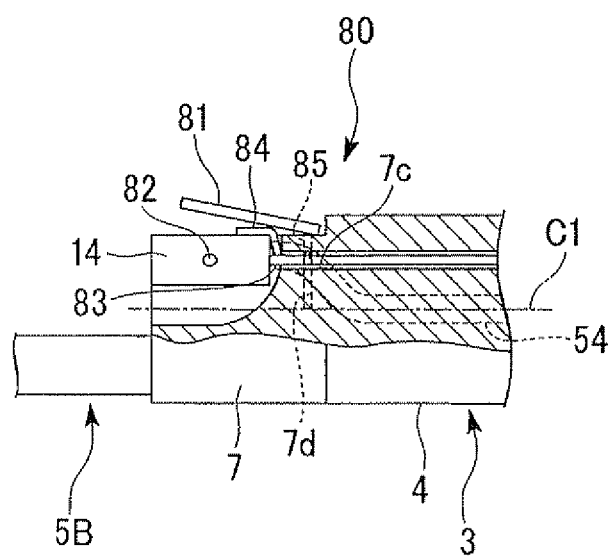
FIG. 13 a sectional view showing the principal portions of the insertion part of the endoscope device according to the third embodiment of the present invention.

The observation main body 14 is supported in the distal end construction part 7 by a pin 82 so as to freely rotate around the direction crossing the axis C1. As shown in FIG. 13, a first wire 83 is fixed to the proximal surface of the observation main body 14 and a second wire 84 is fixed to the side surface of the observation main body 14. The first and second wires 83 and 84 are inserted into the insertion part 3 through a wire guide hole 7c formed in the distal end construction part 7, and are fixed to an operating lever (not shown) provided in the operating part 2. By rotating the operating lever, either of the first or second wire 83 or 84 is pulled.

Two tube-shaped support members 85 are provided such that one end each thereof is fixed to the reflection member 81 and the other ends thereof are moved within reflection member guide holes 7d formed in the distal end construction part 7. By means of a pinion gear (not shown) fixed to the observation main body 14 so as to be coaxial with the pin 82 and a rack gear (not shown) formed in the support member 85, the observation main body 14 and the reflection member 81 move together as follows. That is, the reflection member 81 protrudes so as to reflect an image of the treatment tools 8A and 8B onto the observation main body 14 when the observation main body 14 faces the moving direction G1 opposite to the first and second arm members 5A and 5B in the radial direction, and the reflection member 81 is moved toward the distal portion of the insertion part 3 when the observation main 14 faces the front of the insertion part 3.

The pin 82, the first wire 83, the second wire 84, and the operating lever constitute the above-described observation main body rotation mechanism 80.

It is preferable that the image which is reflected by the reflection member 81 and then is observed by using the observation main body 14 be vertically inverted to be displayed on the monitor.

Next, a method for treating an affected area with the endoscope device 86 constituted as above is described as follows.

Figure 14:
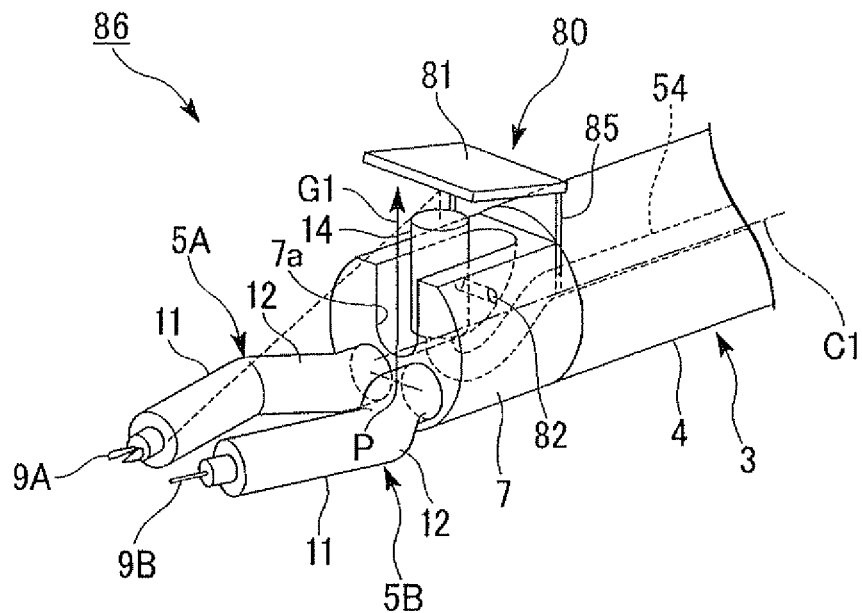
FIG. 14 shows a treatment method with the endoscope device according to the third embodiment of the present invention.

The treatment method of the present embodiment is basically the same as that of the first embodiment. As shown in FIG. 12, the insertion part 3 is inserted into the body cavity in a state where the observation main 14 faces the front and is moved toward the distal portion of the insertion part 3 so as to be housed within the insertion part 3. Then, when making the distal ends of the two arm members 5A and 5B opposed to the affected area, as shown in FIG. 14, the observation main body 14 is turned to face the moving direction G1 by rotating the operating lever to pull the second wire 84 after the second bending parts 12 of the first and second arm members 5A and 5B are fixed in a bending state. At the same time, the reflection member 81 is protruded so as to reflect the image of the treatment tools 8A and 8B onto the observation main body 14.

As described above, according to the endoscope device 86 of the present embodiment, the observation main body 14 can obtain the image of the treatment parts 9A and 9B reflected by the reflection member 81, which is an image seen from the direction more skewed with respect to the axis C1 than a direct image from the treatment parts 9A and 9B to the observation main body 14. Therefore, since the image obtained by the observation main body 14 being interrupted by the proximal portions of the first and second arm members 5A and 5B can be prevented, visibility of the treatment parts 9A and 9B can be improved.

Figure 15:
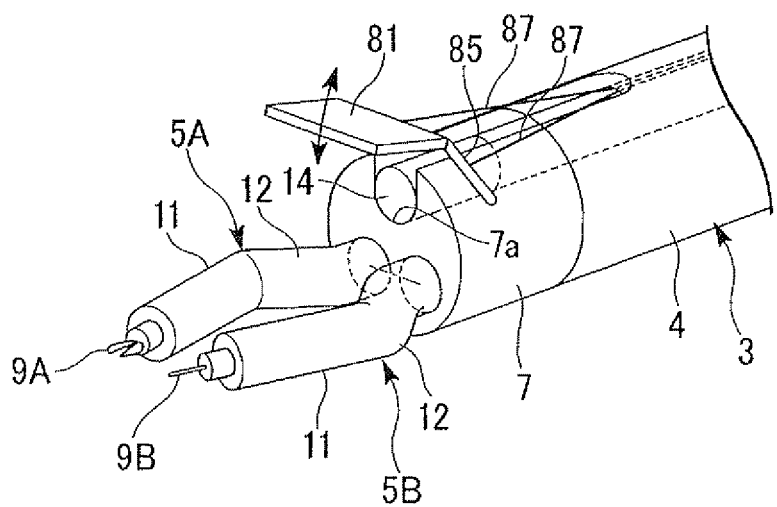
FIG. 15 shows an insertion part of an endoscope device according to a modification example of the third embodiment of the present invention.

As shown in a modification example of the present embodiment in FIG. 15, the observation main body 14 may be fixed to the first groove 7a of the distal end construction part 7, and the two support members 85 may be provided such that one end each thereof is fixed to the reflection member 81, the other ends thereof are rotatively fixed to the distal end construction part 7, and substantially center portions thereof are fixed to distal ends of a pair of operating wires 87. According to this constitution, by pushing and pulling the operating wires 87 from the proximal side to adjust the angle of the reflection member 81, the observation main body 14 can observe not only the direct image from the treatment parts 9A and 9B to the observation main body 14 but also the image which is once reflected by the reflection member 81 and then proceeds to the observation main body 14. Therefore, the treatment parts 9A and 9B can be observed from two angles at once by using the observation main body 14.

Fourth Embodiment

Next, a fourth embodiment of the present invention will be described. Elements the same as those of the first through third embodiments and the modification examples thereof are denoted by the same reference numerals and the descriptions thereof are omitted, and only different points are described.

Figure 16:
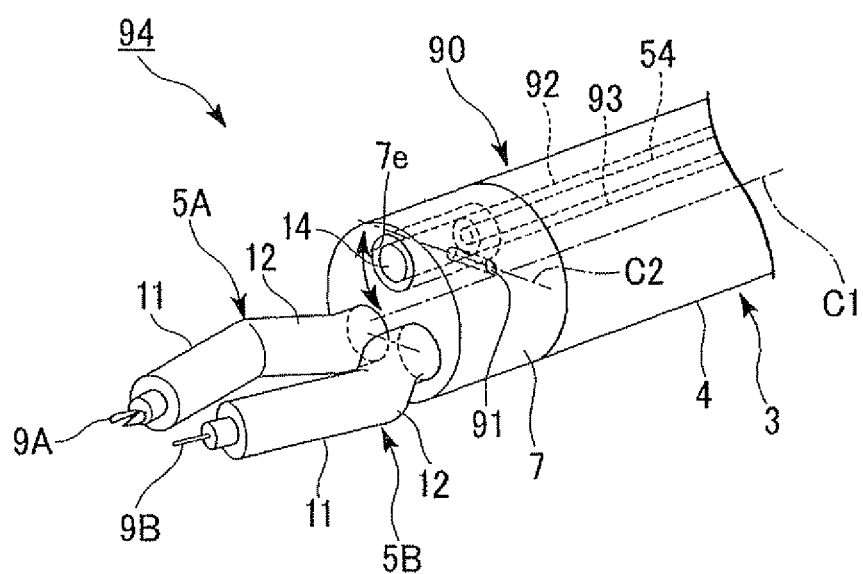
FIG. 16 shows an insertion part of an endoscope device according to a fourth embodiment of the present invention.

As shown in FIG. 16, an endoscope 94 of the present embodiment is provided with an observation main body rotation mechanism 90 which rotates the observation main body 14 around the rotational axis C2 crossing the axis C1 of the insertion part 3 so as to make the distal portions of the first and second arm members 5A and 5B (i.e., the treatment parts 9A and 9B) positioned in the center of view via the observation main body 14.

The observation main body 14 is supported by a pin 91 within a hole 7e formed in the distal end construction part 7 along the axis C1 so as to freely rotate about the rotational axis C2. One end of the proximal surface of the observation main body 14 is fixed to a first wire 92 and the other end of the proximal end surface of the observation main body 14 is fixed to a second wire 93 so as to sandwich the rotational axis C2. The first and second wires 92 and 93 are inserted into the insertion part 3 and are fixed to an operating wire (not shown) provided in the operating part 2. By rotating the operating lever, either of the first or second wire 92 or 93 is pulled.

Next, a method for treating an affected area with the endoscope device 94 constituted as above is described as follows.

The treatment method of the present embodiment is basically the same as that of the first embodiment. However, in the present embodiment, after the second bending parts 12 of the first and second arm members 5A and 5B are fixed in a bending state, the treatment is performed while rotating the observation main body 14 about the rotational axis C2 by rotating the operating lever to adjust the view via the observation main body 14.

As described above, according to the endoscope device 94 of the present embodiment, it is possible to make the treatment parts 9A and 9B positioned in the center of view via the observation main body 14 by rotating the observation main body 14 about the rotational axis C2 crossing the axis C1. As a result, it is possible to adjust the view via the observation main body 14 such that the operator easily observes.

Fifth Embodiment

Next, a fifth embodiment of the present invention will be described. Elements the same as those of the first through fourth embodiments and the modification examples thereof are denoted by the same reference numerals and the descriptions thereof are omitted, and only different points are described.

Figure 17:
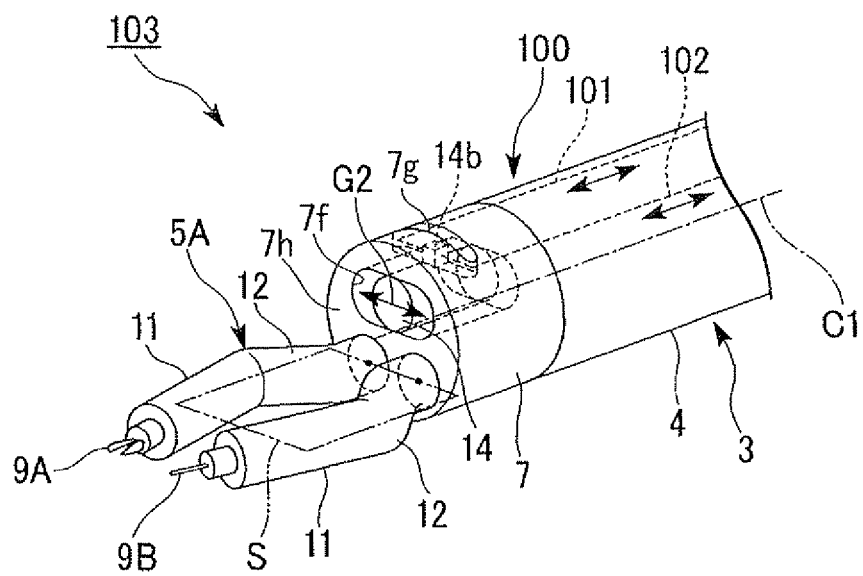
FIG. 17 shows an insertion part of an endoscope device according to a fifth embodiment of the present invention.
Figure 18:
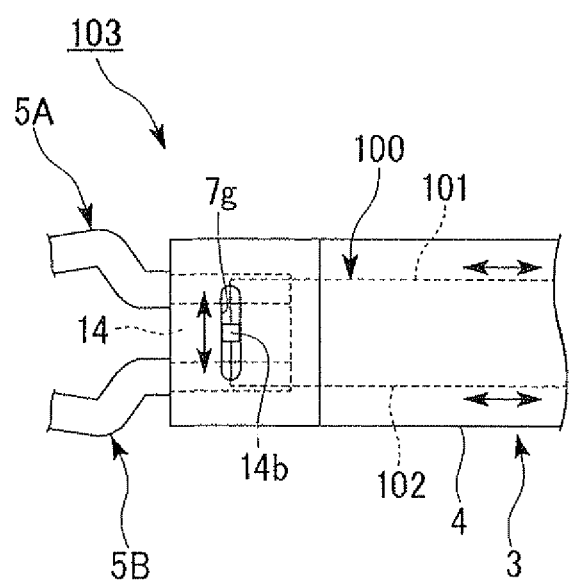
FIG. 18 is a plan view of the insertion part of the endoscope device according to the fifth embodiment of the present invention.

As shown in FIGS. 17 and 18, an endoscope device 103 of the present embodiment is provided with an observation main body moving mechanism 100 which moves the observation main body 14 in the moving direction G2 parallel to an arm plane S on which the arm members 5A and 5B are attached, so as to position the distal portions of the first and second arm members 5A and 5B (i.e., the treatment parts 9A and 9B) in the center of view via the observation main body 14.

As shown in FIG. 17, the arm plane S on which the arm members 5A and 5B are attached is a plane which includes positions where the arm members 5A and 5B are provided on the distal end surface 7h of the distal end construction part 7 and which is parallel to the axis C1.

A first long hole 7f is formed on the distal end surface 7h of the distal end construction part 7 along the moving direction 62 in which the observation main body 14 moves, and a second long hole 7g is formed on the side surface of the distal end construction part 7 so as to be parallel to the moving direction G2. The first and second long holes 7f and 7g communicate with each other inside the distal end construction part 7.

The observation main body 14 is provided in the first long hole 7h with a protrude portion 14b formed in the observation main body 14 engaged with the second long hole 7g such that the observation main body 14 is able to move only in the moving direction G2. A distal end of a first wire 101 is fixed to the surface of one side of the protrude portion 14b in the moving direction G2, and a distal end of a second wire 102 is fixed to the surface of the other side of the protrude portion 14b. The first and second wires 101 and 102 are inserted into the insertion part 3 and are fixed to an operating wire (not shown) provided in the operating part 2. By rotating the operating lever, either of the first or second wire 101 or 102 is pulled.

Next, a method for treating an affected area with the endoscope device 103 constituted as above is described as follows.

The treatment method of the present embodiment is basically the same as that of the first embodiment. However, in the present embodiment, after the second bending parts 12 of the first and second arm members 5A and 5B are fixed in a bending state, the treatment is performed while moving the observation main body 14 in the moving direction G2 by rotating the operating lever to adjust the view via the observation main body 14.

As described above, according to the endoscope device 103 of the present embodiment, it is possible to make the treatment parts 9A and 9B positioned in the center of view via the observation main body 14 by moving the observation main body 14 in the moving direction G2. As a result, it is possible to adjust the view via the observation main body 14 such that the operator easily observes.

Sixth Embodiment

Next, a sixth embodiment of the present invention will be described. Elements the same as those of the first through fifth embodiments and the modification examples thereof are denoted by the same reference numerals and the descriptions thereof are omitted, and only different points are described.

Figure 19:
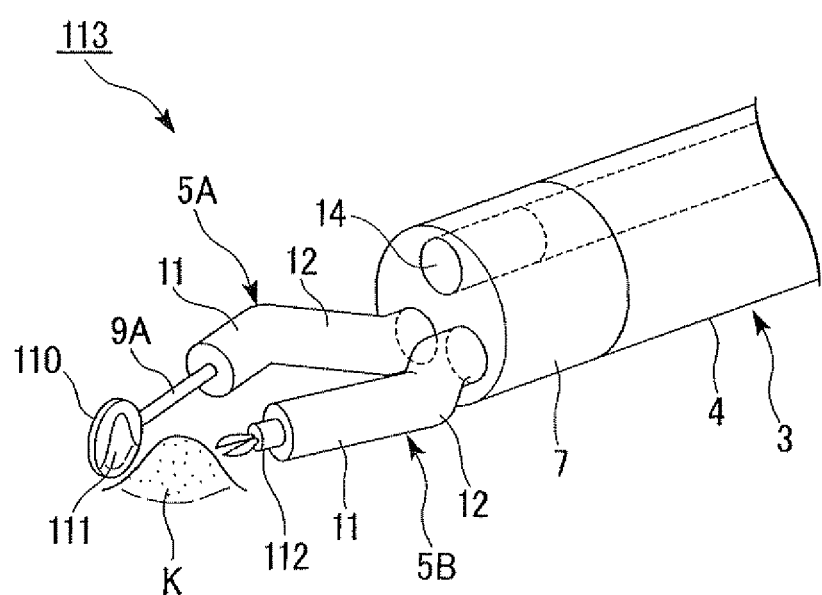
FIG. 19 shows an insertion part of an endoscope device according to a sixth embodiment of the present invention.

As shown in FIG. 19, an endoscope device 113 of the present embodiment is provided with a reflection member 110 in the first arm member 5A which reflects the image of a desired site K such as an affected area toward the observation main body 14.

One surface of the reflection member 110 is provided with a mirror 111 which reflects a light. Though the reflection member 110 is provided in the treatment part 9A of the treatment tool 8A in the present embodiment, the reflection member 110 may be provided in the distal portion of the first arm member 5A. Furthermore, in the present embodiment, a gripping forceps is employed as a treatment tool 112.

Next, a method for treating an affected area with the endoscope device 113 constituted as above is described as follows.

The treatment method of the present embodiment is basically the same as that of the first embodiment. However, in the present embodiment, after the second bending parts 12 of the first and second arm members 5A and 5B are fixed in a bending state, the reflection member 110 is moved to a position to be observed in the vicinity of the desired site K while bending the first bending part 11 of the first arm member 5A by rotating the operating stick 31A. Then, the desired site K is removed by the treatment tool 112 by moving the slider 35B while bending the first bending part 11 of the second arm member 5B by rotating the operating stick 31B.

As described above, according to the endoscope device 113 of the present embodiment, the desired site K and the vicinity thereof can be observed by changing the direction of the reflection member 110 or moving the reflection member 110 in order to easily observe the desired site K. Furthermore, the condition and the treatment state of the desired site K can be observed more precisely from two directions.

Though the reflection member 110 is provided only in the first arm member 5A in the present invention, the reflection member 110 may be provided only in the second arm member 5B and the reflection members 110 may be provided in both of the first and second arm members 5A and 5B.

Next, a first modification example of the sixth embodiment of the present invention will be described. Elements the same as those of the first through sixth embodiments and the modification examples thereof are denoted by the same reference numerals and the descriptions thereof are omitted, and only different points are described.

Figure 20:
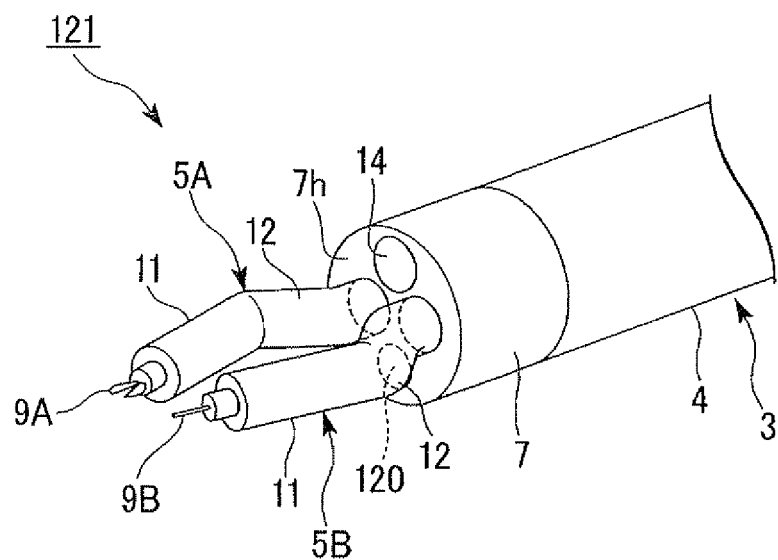
FIG. 20 shows an insertion part of an endoscope device according to a first modification example of the sixth embodiment of the present invention.

As shown in FIG. 20, an endoscope device 121 of the present modification example is provided with a sub-observation main body 120 in the distal end surface 7h of the distal end construction part 7 at a position opposite to the observation main body 14 with respect to the first and second arm members 5A and 5B. Similar to the observation main body 14, the sub-observation main body 120 houses a light receiving element such as a lens and a CCD and connects to a sub-observation cable (not shown) which transmits an image obtained by the sub-observation main body 120 to the monitor.

The monitor is constructed such that the displayed image can be switched between an image obtained by the observation main body and an image obtained by the sub-observation main body 120 while observing the position of the treatment parts 9A and 9B or the first and second arm members 5A and 5B.

As described above, according to the endoscope device 121 of the present modification example, since the treatment tools 9A and 9B can be observed from the two directions by using the observation main body 14 and the sub-observation main body 120, visibility of the treatment parts 9A and 9B can be improved.

Next, a second modification example of the sixth embodiment of the present invention will be described. Elements the same as those of the first through sixth embodiments and the modification examples thereof are denoted by the same reference numerals and the descriptions thereof are omitted, and only different points are described.

Figure 21:
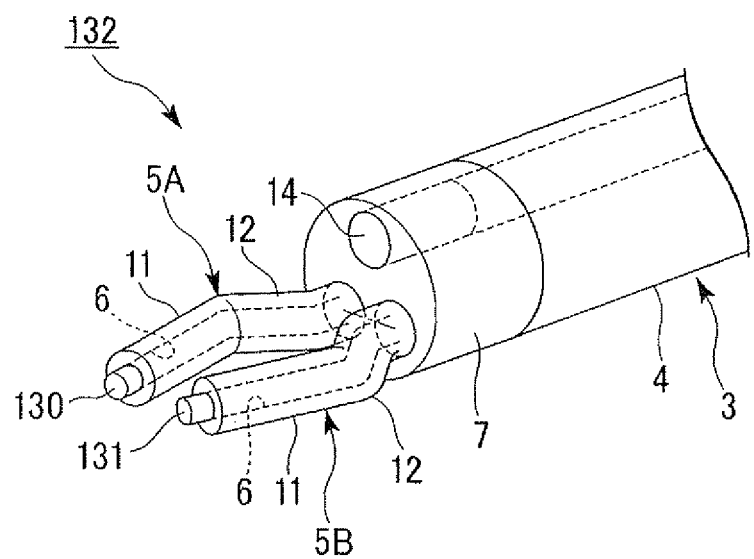
FIG. 21 shows an insertion part of an endoscope device according to a second modification example of the sixth embodiment of the present invention.

As shown in FIG. 21, in the present modification example, sub-endoscopes 130 and 131 are inserted into the instrument channels 6 of the first and second arm members 5A and 5B respectively. Images obtained from the sub-endoscopes 130 and 131 are transmitted to the monitor via sub-endoscope cables (not shown). The monitor is constructed so as to switch between the states such as where only an image obtained by the observation main body 14 is displayed or where images obtained not only by the observation main body but also by the sub-endoscopes 130 and 131 are displayed all together.

In the present modification example, the sub-endoscopes 130 and 131 can be exchanged for treatment tools such as a gripping forceps and an injection instrument if necessary.

As described above, according to the endoscope device 132 of the present modification example, since the treatment tools 9A and 9B can be observed from the three directions by using the observation main body 14, the sub-endoscope 130, and the sub-endoscope 131, visibility of the treatment parts 9A and 9B and the arm members 5A and 5B can be improved.

Next, a third modification example of the sixth embodiment of the present invention will be described. Elements the same as those of the first through sixth embodiments and the modification examples thereof are denoted by the same reference numerals and the descriptions thereof are omitted, and only different points are described.

Figure 22:
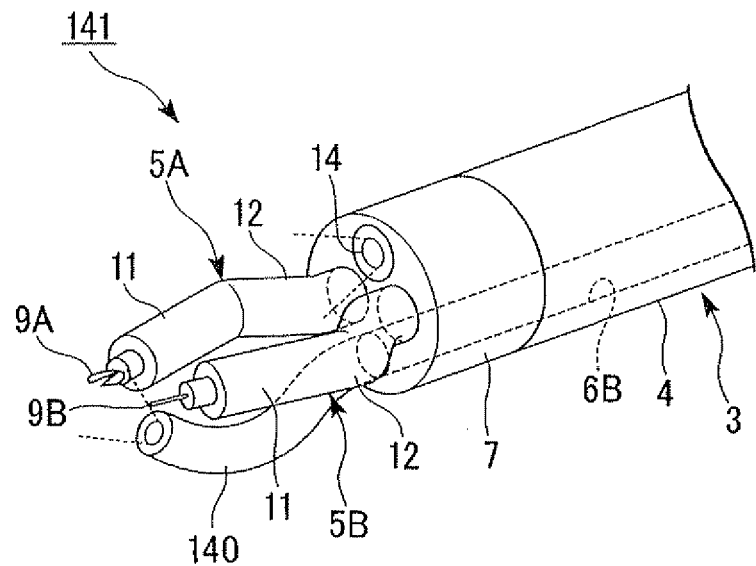
FIG. 22 shows an insertion part of an endoscope device according to a third modification example of the sixth embodiment of the present invention.

As shown in FIG. 22, in the present modification example, a sub-channel 6B is formed in the insertion part 3, and a sub-endoscope 140 the distal portion of which is bendable is inserted into the sub-channel 6B so as to freely advance and retract in the direction of the axis C1. An image obtained by the sub-endoscope 140 is transmitted to the monitor via a sub-endoscope cable (not shown). The monitor is constructed so as to switch between the states such as where only an image obtained by the observation main body 14 is displayed or where images obtained not only by the observation main body but also by the sub-endoscope 140 are displayed all together.

As described above, according to the endoscope device 141 of the present modification example, since the treatment tools 9A and 9B can be observed by using the observation main body 14 and the sub-endoscope 140, visibility of the treatment parts 9A and 9B can be improved. Furthermore, since the sub-endoscope 140 is formed such that the distal portion thereof is bendable and freely advances and retracts in the direction of the axis C1, visibility of the treatment parts 9A and 9B can be improved higher.

Next, a fourth modification example of the sixth embodiment of the present invention will be described. Elements the same as those of the first through sixth embodiments and the modification examples thereof are denoted by the same reference numerals and the descriptions thereof are omitted, and only different points are described.

Figure 23:
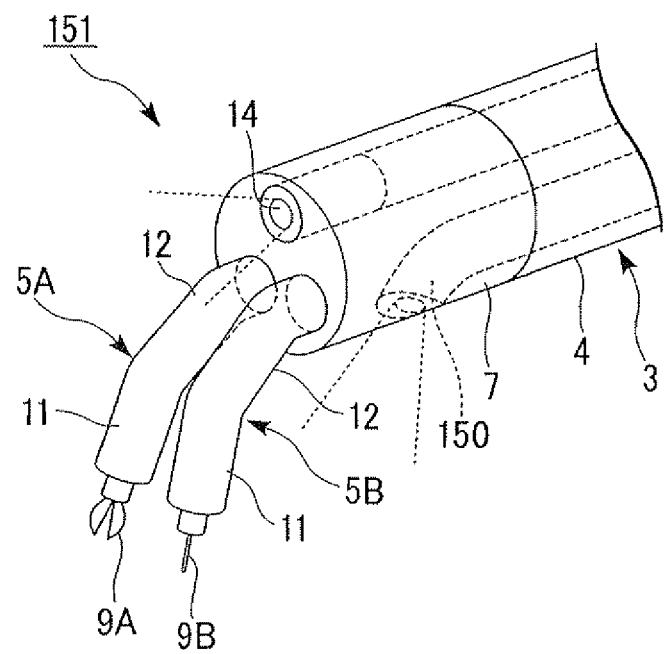
FIG. 23 shows an insertion part of an endoscope device according to a fourth modification example of the sixth embodiment of the present invention.

As shown in FIG. 23, in the modification example, a sub-endoscope 150 which observes in a front diagonal direction is provided on the outer circumferential surface of the distal end construction part 7. An image obtained by the sub-endoscope 150 is transmitted to the monitor via a sub-endoscope cable (not shown). The monitor is constructed so as to switch between the states such as where only an image obtained by the observation main body 14 is displayed or where images obtained not only by the observation main body but also by the sub-endoscope 150 are displayed all together.

As described above, according to the endoscope device 151 of the present modification example, since the treatment tools 9A and 9B can be observed by using the observation main body 14 and the sub-endoscope 150, field of view can be increased and visibility of the treatment parts 9A and 9B can be improved.

Seventh Embodiment

Next, a seventh embodiment of the present invention will be described. Elements the same as those of the first through sixth embodiments and the modification examples thereof are denoted by the same reference numerals and the descriptions thereof are omitted, and only different points are described.

Figure 24:
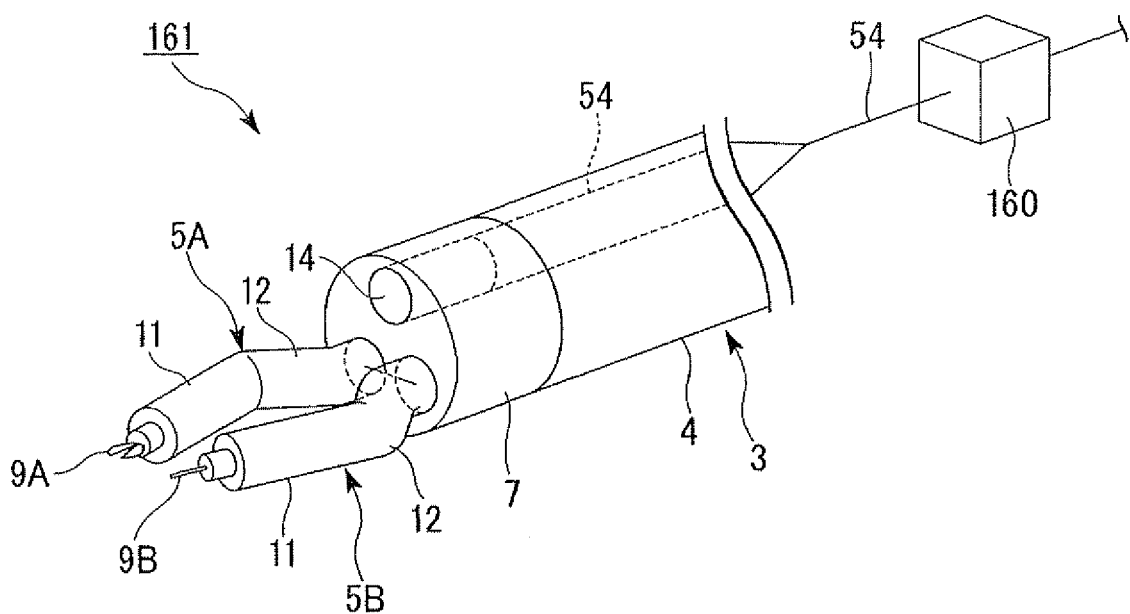
FIG. 24 shows an insertion part of an endoscope device according to a seventh embodiment of the present invention.

As shown in FIG. 24, an endoscope device 161 of the present embodiment is provided with an image processor 160 which extracts an image showing the distal portions of the first and second arm members 5A and 5B (i.e., the treatment parts 9A and 9B) and the vicinity thereof from an image obtained by the observation main body 14, and a not-shown monitor (display portion) which magnifies and displays the image extracted by the image processor 160. In the present embodiment, it is preferable that the treatment parts 9A and 9B and the arm members 5A and 5B be painted a color having less redness.

The image processor 160 has functions such as extracting a specified color in an image captured by the endoscope unit 14, binarizing the brilliances of the light based on a properly determined threshold, and extracting the outline of a specified color in the image to recognize the distal portions.

Figure 25:
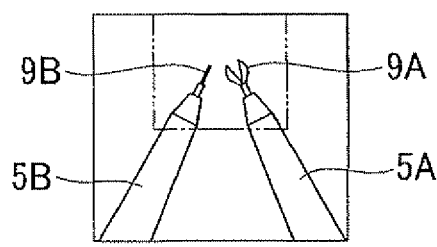
FIG. 25 is an image of treatment parts before magnification displayed on a monitor according to the seventh embodiment of the present invention.
Figure 26:
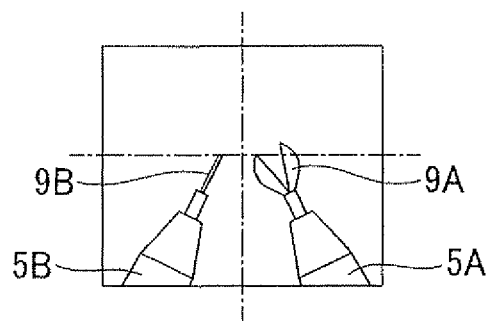
FIG. 26 is an image of the treatment parts after magnification displayed on the monitor according to the seventh embodiment of the present invention.

In the process of the image processor 160, firstly, the red light is extracted in an image (shown in FIG. 25) captured by the endoscope unit 14 to measure brilliances of the red light, and then the brilliances are binarized based on a properly determined threshold since the tissues inside the body cavity have a reddish color. As a result, the shapes of the treatment tools 9A and 9B can be extracted from the tissue image such that, for example, the tissue is colored black and the treatment parts 9A and 9B are colored white. Furthermore, shapes of the outline of the black portion and white portion are extracted, and then positions where the direction of the shape of the outline changes by more than a predetermined value are detected as the position of the treatment parts 9A and 9B. When the image processor 160 detect the position of the treatment parts 9A and 9B, an image shown in FIG. 26 into which the original image is magnified by two, for example, with the middle position of the treatment parts 9A and 9B as a center, is transmitted and displayed on the monitor.

As described above, according to the endoscope device 161 of the modification example, since the treatment parts 9A and 9B can be magnified and then displayed on the monitor, visibility of the treatment parts 9A and 9B can be improved.

A mechanism for optically magnifying an image may be housed within the observation main body 14.

Eighth Embodiment

Next, an eighth embodiment of the present invention will be described. Elements the same as those of the first through seventh embodiments and the modification examples thereof are denoted by the same reference numerals and the descriptions thereof are omitted, and only different points are described.

Figure 27:
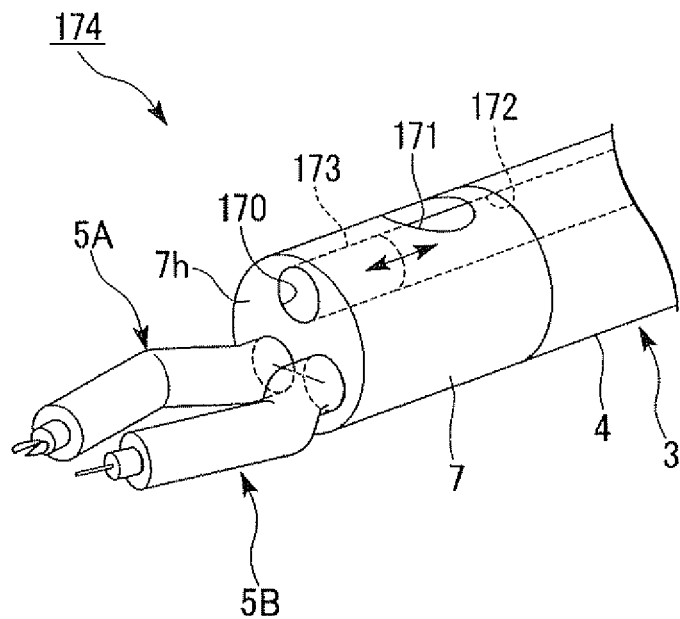
FIG. 27 shows an insertion part of an endoscope device according to an eighth embodiment of the present invention.

As shown in FIG. 27, an endoscope device 180 of the present embodiment is provided with a channel 172 formed in the distal end construction part 7, and an observation mechanism 173 the distal portion of which is bendable and which is inserted into the channel 172. The distal portion of the channel 172 is communicated both with a first opening 170 formed on the distal end surface 7h of the distal end construction part 7 and with a second opening 171 formed on the side surface of the distal end construction part 7. The observation mechanism 173 is capable of observation from the first opening 170 and the second opening 171. The distal portion of the observation mechanism 173 is bendable by an operating wire (not shown) provided inside thereof.

In order to enhance the insertion ability of the observation mechanism 173, it is preferable that the second opening 171 open toward a front diagonal direction of the distal end construction part 7.

When an affected area is treated with the endoscope device 174 constituted as above, the insertion part 3 is inserted into the body cavity of the subject while observing the front of the insertion part 3 with the observation mechanism 173 straight and inserted into the first opening 170. When the first and second arm members 5A and 5B reach the affected area and the treatment is performed at the front of the distal end construction part 7, as shown in FIG. 27, the treatment is performed in a state where the observation mechanism 173 is inserted into the first opening 170 with the arm members 5A and 5B extending forward.

Figure 28:
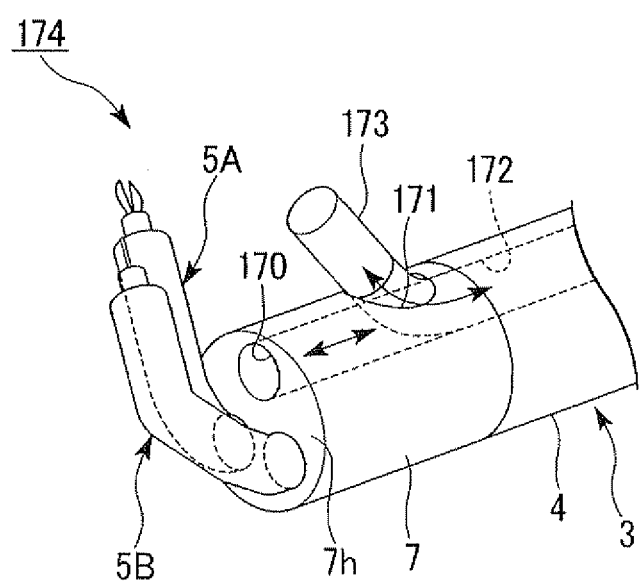
FIG. 28 shows a treatment method with the endoscope device according to the eighth embodiment of the present invention.

When the treatment is performed at the outside in the radial direction of the distal end construction part 7, as shown in FIG. 28, the observation mechanism 173 is once pulled back to the communicating portion of the first opening 170 and the second opening 171 and then is pushed toward the distal side with the distal portion of the observation mechanism 173 bent toward the second opening 171. Then, the arm members 5A and 5B are bent toward the second opening 171 and the treatment is performed by the arm members 5A and 5B while observing by the observation mechanism 173 from the second opening 171 side.

As described above, according to the endoscope device 174 of the present embodiment, since it is possible to observe by using the observation mechanism 173 not only the front of the distal end construction part 7 but also the outside in the radial direction of the distal end construction part 7, the observable area of the treatment parts 9A and 9B by using the one observation mechanism 173 can be expanded.

Known endoscopes may be employed as the observation mechanism 173.

Next, a modification example of the eighth embodiment of the present invention will be described. Elements the same as those of the first through eighth embodiments are denoted by the same reference numerals and the descriptions thereof are omitted, and only different points are described.

Figure 29:
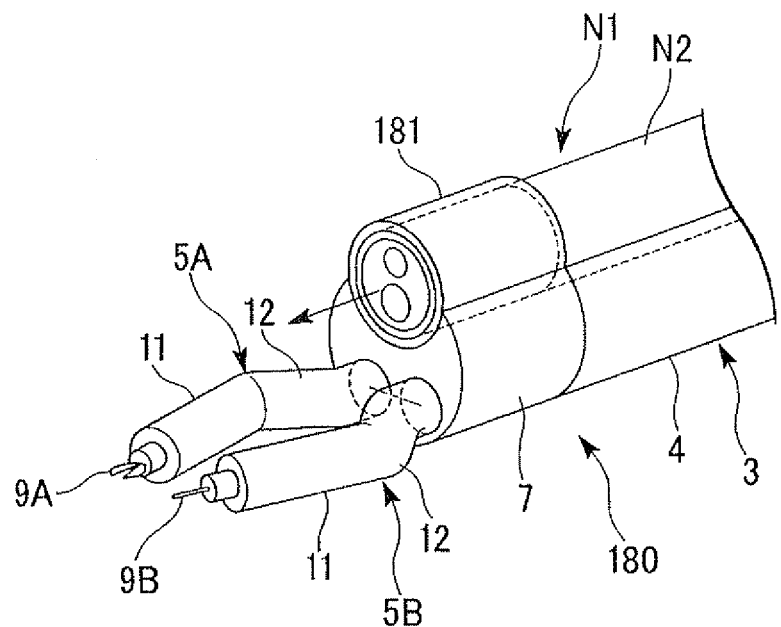
FIG. 29 shows an insertion part of an endoscope device according to a modification example of the eighth embodiment of the present invention.

As shown in FIG. 29, in the present modification example, the observation main body 14 is not provided in an endoscope device 180. Instead, a known endoscope N1 which is not provided with a treatment part is used with the endoscope N1 attached to a cylindrical guide member 181 provided at the distal end construction part 7 of the endoscope device 180.

The endoscope device 180 may be inserted into the body cavity of the subject such that the endoscope N1 is inserted into the body cavity in advance, and then the endoscope device 180 is inserted by moving the guide member 181 along an insertion part N2 of the endoscope N1.

Figure 30:
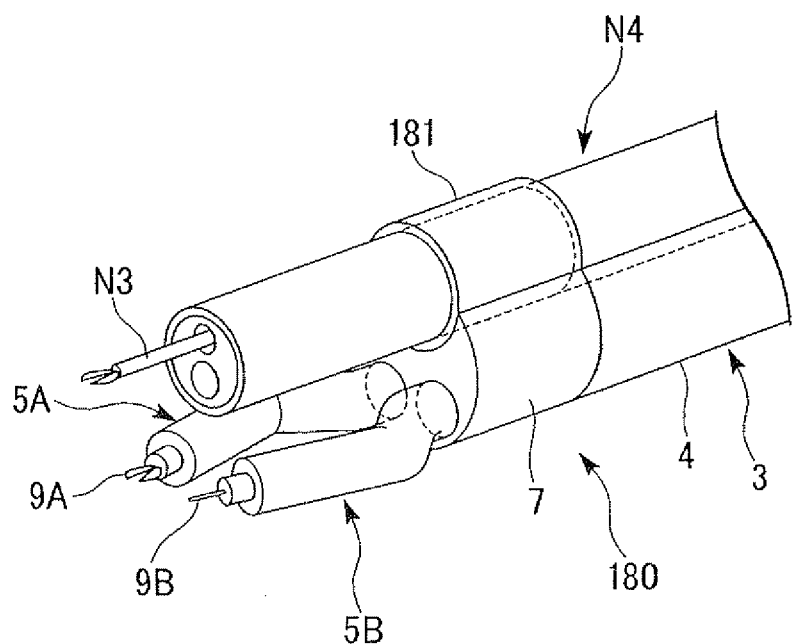
FIG. 30 shows an insertion part of an endoscope device according to another modification example of the eighth embodiment of the present invention.

As shown in FIG. 30, the endoscope device 180 may be attached to an endoscope N4 provided with a treatment part N3.

As described above, according to the endoscope device 180 of the present embodiment, the treatment can be performed while observing forward with a known endoscope instead of the observation main body 14.

Ninth Embodiment

Next, a ninth embodiment of the present invention will be described. Elements the same as those of the first through eighth embodiments and the modification examples thereof are denoted by the same reference numerals and the descriptions thereof are omitted, and only different points are described.

Figure 31:
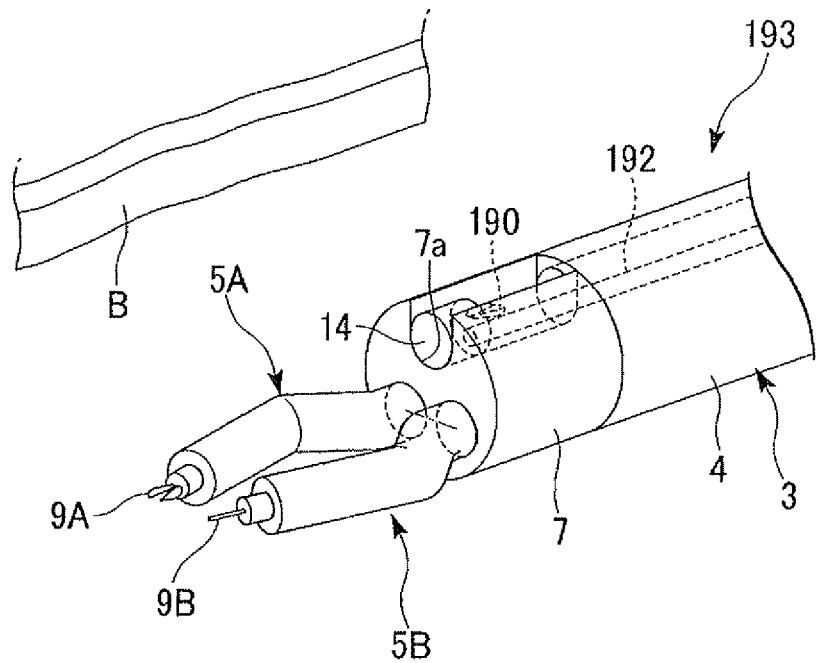
FIG. 31 shows an insertion part of an endoscope device according to a ninth embodiment of the present invention.
Figure 32:
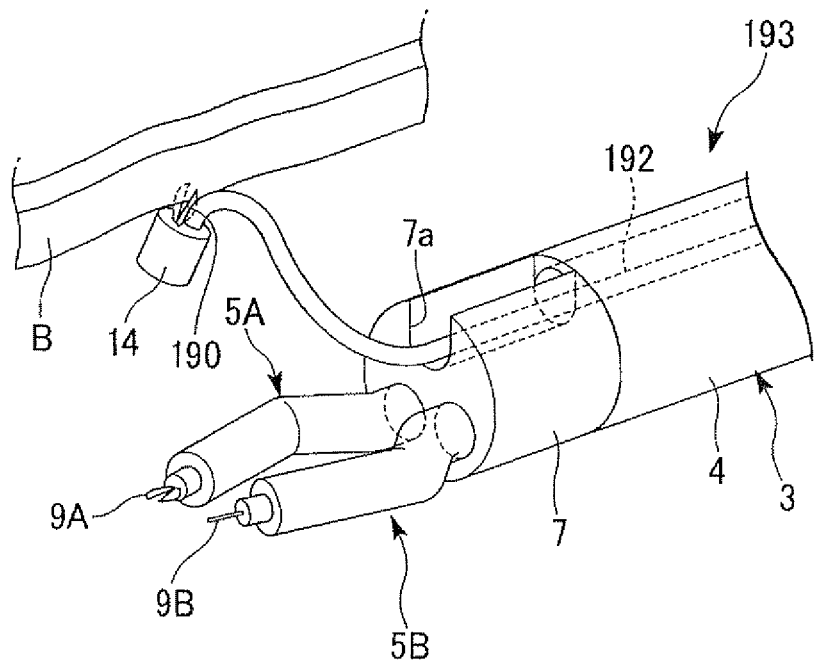
FIG. 32 shows a treatment method with the endoscope device according to the ninth embodiment of the present invention.

As shown in FIG. 31, in the present embodiment, an endoscope device 193 is provided with the observation main body 14 disposed so as to freely separate from the distal end construction part 7, an attachment member 190 provided in the observation main body 14 for attaching the observation main body 14 to the inner wall B of the body cavity such as the abdominal wall in a freely attaching and detaching manner, and a treatment tool 191 for attachment inserted into the first arm member 5A. The treatment tool 191 for attachment is capable of attaching the observation main body 14 to the inner wall B of the body cavity by the attachment member 190 by engaging with the observation main body 14 disposed in the distal end construction part 7.

Though a clip which has a spring and grasps the inner wall B of the body cavity is employed as the attachment member 190 in the present embodiment, a hook, a magnet or the like may be employed as long as it can attach the observation main body 14 to the inner wall B of the body cavity.

A cable 192 connects the observation main body 14 and the insertion part 3. The observation main body 14 is hosed within the first groove 7a by reeling up the cable 192 by using a reeling mechanism (not shown) provided in the proximal portion of the cable 192.

Next, a method for treating an affected area with the endoscope device 193 constituted as above is described as follows.

The treatment method of the present embodiment is basically the same as that of the first embodiment. However, in the present embodiment, after the insertion part 3 is inserted into the body cavity with the two arm members 5A and 5B opposed to the affected area, the first bending part 11 of the first arm member 5A is bent such that the treatment tool 191 for attachment is engaged with the observation main body 14. Then, the observation main body 14 is attached to the inner wall B of the body cavity by the attachment member 190 while extending the cable 192.

As described above, according to the endoscope device 193 of the present modification example, the treatment parts 9A and 9B can be observed from the skew direction, not from the proximal side of the first and second arm members 5A and 5B. As a result, since it can be prevented that the field of view via the observation main body 14 is interrupted by the proximal portions of the first and second arm members 5A and 5B when performing the treatment, visibility of the treatment parts 9A and 9B can be improved.

While preferred embodiments of the invention have been described and illustrated above, it should be understood that these are exemplary examples of the invention and are not to be considered as limiting. Additions, omissions, substitutions, and other modifications can be made without departing from the spirit or scope of the present invention.

Though the first and second arm members 5A and 5B are provided in the distal end surface 7h of the distal end construction part 7 in the first through ninth embodiments and the modification examples thereof for example, the first and second arm members 5A and 5B may be provided in the side surface of the distal end construction part 7.

Though the two first and second arm members 5A and 5B are provided in the distal end surface 7h of the distal end construction part 7 in the first through forth embodiments, the sixth through ninth embodiments, and the modification examples thereof, for example, three or more arm members may be provided.

The invention is not to be considered as being limited by the foregoing description, and is only limited by the scope of the appended claims.

What is claimed is:

1. An endoscope device comprising:
    an elongated tubular insertion part;
    a plurality of arm members provided in a distal portion of the insertion part so as to protrude forward, the plurality of arm members being capable of treatment with a treatment tool inserted thereinto;
    an observation cable comprising an energization member that is inserted into the insertion part and having a bending tendency, and an observation main body provided in the distal portion of the energization member, wherein the bending tendency of the energization member is capable of restoring to a bent shape in which the energization member bends so as to dispose the observation main body toward the direction opposite to the plurality of arm members in the radial direction of the insertion part; and
    a holding-down member provided on an outer surface of the insertion part so as to freely move along a circumferential direction of the outer surface of the insertion part with respect to the insertion part, the holding-down member being configured to hold down the energization member in a radially inward direction of the insertion part so as to deform the bent shape of the energization member into a linear shape that is along a longitudinal axis of the insertion part;
    wherein by moving the holding-down member to a position other than the position where the holding-down member holds down the energization member in the radially inward direction of the insertion part, the energization member is capable of being restored to the bent shape in which the observation main body is disposed in a position separated from the insertion part in a radially outward direction while the plurality of arm members is kept within a observable range of view of the observation main body.

* * * * *